United States Patent
Chiba et al.

(10) Patent No.: US 7,084,268 B1
(45) Date of Patent: Aug. 1, 2006

(54) CARBAPENEM COMPOUND CRYSTALS AND INTERJECTION PREPARATIONS

(75) Inventors: Hiroyuki Chiba, Ibaraki (JP); Masahiko Tsujii, Chiba (JP); Astsushi Koiwa, Ibaraki (JP); Shin Sakurai, Chiba (JP); Akio Kayano, Ibaraki (JP); Hiroyuki Ishizuka, Ibaraki (JP); Hiroyuki Saito, Ibaraki (JP); Taiju Nakamura, Ibaraki (JP); Ikuo Kushida, Ibaraki (JP); Yasuyuki Suzuki, Ibaraki (JP); Takako Yoshiba, Ibaraki (JP); Kazuhide Ashizawa, Ibaraki (JP); Masahiro Sakurai, Ibaraki (JP); Eiichi Yamamoto, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 701 days.

(21) Appl. No.: 09/979,679

(22) PCT Filed: Jun. 5, 2000

(86) PCT No.: PCT/JP00/03642

§ 371 (c)(1),
(2), (4) Date: Nov. 16, 2001

(87) PCT Pub. No.: WO00/75143

PCT Pub. Date: Dec. 14, 2000

(30) Foreign Application Priority Data

Jun. 3, 1999 (JP) .................................. 11-156810
May 25, 2000 (JP) .............................. 2000-153891

(51) Int. Cl.
*C07D 477/20* (2006.01)
*A61K 31/407* (2006.01)
*A61P 31/04* (2006.01)

(52) U.S. Cl. .................................................. 540/350

(58) Field of Classification Search .......... 514/210.12; 540/350
See application file for complete search history.

(56) References Cited

U.S. PATENT DOCUMENTS

| | | | | |
|---|---|---|---|---|
| 6,007,810 A | * | 12/1999 | Ishikawa et al. | 424/94.61 |
| 6,077,829 A | * | 6/2000 | Tanaka et al. | 514/12 |
| 6,100,047 A | * | 8/2000 | Wilkison et al. | 435/7.1 |
| 6,218,550 B1 | * | 4/2001 | Suzuki et al. | 548/400 |

FOREIGN PATENT DOCUMENTS

| | | |
|---|---|---|
| EP | 0 256 377 | 2/1988 |
| EP | 0 773 222 A1 | 5/1997 |
| JP | 1-268688 | 10/1989 |
| JP | 8-73462 | 3/1996 |
| JP | 10-152491 | 6/1998 |
| JP | 10-195076 | 7/1998 |
| WO | WO98/52918 | 11/1998 |
| WO | WO 9906365 A1 * | 2/1999 |

OTHER PUBLICATIONS

Journal of Medicinal Chemistry, vol. 22, No. 12, Dec., 1979; *Communications to the Editor*, pp. 1435-1436 (2 sheets).

* cited by examiner

*Primary Examiner*—Mark L. Berch
(74) *Attorney, Agent, or Firm*—Flynn, Thiel, Boutell & Tanis, P.C.

(57) ABSTRACT

The present invention provides carbapenem hydrochloride trihydrate crystals, which are chemically stable, easily purified and useful as antimicrobial agents, a process for producing them, and a powdery charged preparation for injection containing them. That is, it provides carbapenem hydrochloride trihydrate crystals having a powdery X-ray diffraction pattern containing lattice distances (d) of 9.0, 4.1 and 2.8 Å, a process for producing them, and a powdery charged preparation for injection containing them.

1 Claim, 6 Drawing Sheets

CARBAPENEM COMPOUND CRYSTALS AND INTERJECTION PREPARATIONS

TECHNICAL FIELD

The present invention relates to a salt of a carbapenem compound or hydrate crystals of the salt, a process for producing it, and a powdery charged preparation for injection. The carbapenem compound is useful as an antimicrobial agent and an antibiotic.

PRIOR ART

The carbapenem compound or a salt thereof is known to have a strong and wide antimicrobial spectrum ranging from Gram negative to positive bacteria, but there is a problem with stability thereof in the human body and with safety in the human body owing to its toxicity.

However, JP-A 8-73462 discloses that the carbapenem compound, that is, (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid or a salt thereof is a compound having a strong antimicrobial activity and useful as a pharmaceutical preparation having high safety to the human body.

Further, its hydrochloride is one desirable salt form superior in solubility as a medicine having a strong antimicrobial activity.

Generally for converting a chemical into an injection, it is dissolved, emulsified or dispersed in a liquid such as water to form a liquid injection, or converted into a powdery preparation for injection, which just before use, is dissolved, emulsified or dispersed in a liquid.

However, this carbapenem compound or its hydrochloride is unstable in solution, and the degradation thereof is promoted under heating conditions, so it is hardly formed into a liquid injection.

Further, when the carbapenem compound or its hydrochloride is formed into a freeze-dried preparation frequently used as a powdery injection preparation to be dissolved just before use, the degradation thereof is promoted under heating conditions in the case where e.g. mannitol is used as the major filler in the freeze-dried preparation. Accordingly, it is hardly formed into a freeze-dried preparation.

Further, the carbapenem compound or a salt thereof which was formed by freeze-drying into a powdery charged preparation is amorphous and chemically unstable.

Further, because the carbapenem compound or a salt thereof could not easily be crystallized by techniques at that time, it was finally purified by reverse phase silica gel column chromatography to give an amorphous product. In such column purification, however, a large amount of solvent is used to increase production costs and to make industrial large-scale treatment difficult, and further there are many problems such as possible pyrolysis in concentration of fractions, residual solvent, waste liquor, and environmental pollution resulting from solvent evaporation. In addition, this amorphous substance is instable in solution, so the degradation thereof is promoted under heating conditions, thus making pharmaceutical manufacturing problematic.

Definition of Terms (+)-(1R,5S,6S)-6-[(R)-1-Hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid, or (+)-(4R,5S,6S)-6-[(R)-1-hydroxyethyl]-3-[(2S,4S)-2-[(R)-1-hydroxy-1-[(R)-pyrrolidine-3-yl]methyl]pyrrolidine-4-yl]thio-4-methyl-7-oxo-1-azabicyclo[3.2.0]hept-2-ene-2-carboxylic acid according to nomenclature by IUPAC, is called the carbapenem compound. Salts thereof such as hydrochloride, hydrate crystals of the salts, starting salts for synthesizing them, and other starting compounds having a carbapenem skeleton are called carbapenem derivatives. Examples thereof include (+)-(4R, 5S,6S)-6-[(R)-1-hydroxyethyl]-3-[(2S,4S)-2-[(R)-1-hydroxy-1-[(R)-pyrrolidine-3-yl]methyl]pyrrolidine-4-yl]thio-4-methyl-7-oxo-1-azabicyclo[3.2.0]hept-2-ene-2-carboxylic acid monohydrochloride monohydrate and (+)-(4R,5S,6S)-6-[(R)-1-hydroxyethyl]-3-[(2S,4S)-2-[(R)-1-hydroxy-1-[(R)-pyrrolidine-3-yl]methyl]pyrrolidine-4-yl]thio-4-methyl-7-oxo-1-azabicyclo[3.2.0]hept-2-ene-2-carboxylic acid monohydrochloride trihydrate.

DISCLOSURE OF INVENTION

As a result of further extensive study for solving the problem described above, the present inventors found that among salts of the carbapenem compound, there are monohydrate crystals and trihydrate crystals which are chemically stable crystals and industrially useful compounds easily separated from impurities, and the present invention was thereby completed.

The present invention relates to (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals having a powdery X-ray diffraction pattern containing lattice distances (d) of 9.0, 4.1 and 2.8 Å, represented by formula (1-1):

(1-1)

or monohydrate crystals having a powdery X-ray diffraction pattern containing lattice distances (d) of 5.2, 4.3 and 4.0 Å, represented by formula (1-2):

(1-2)

Preferably, the trihydrate crystals have a powdery X-ray diffraction pattern containing lattice distances (d) of 9.0, 5.4, 5.2, 5.0, 4.1, 4.0, 3.8, 3.6, 3.4, 3.1, 2.8 and 2.6 Å.

The present invention also provides a process for producing the above hydrate crystals. That is, the present invention relates to a process for producing (+)-(1R,5S,6S)-6-[(R)-1- hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals, which comprises dissolving (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid (referred to hereinafter as the carbapenem compound) or a derivative thereof in a solvent system consisting of water and at least one crystallization solvent selected from the group consisting of dimethyl ether, diethylene glycol monomethyl ether, triethylene glycol monomethyl ether, diethylene glycol monoethyl ether, 1-acetoxy-2-methyl ethane, 3-methoxybutanol, 1-ethoxy-2-propanol, 1-methoxy-2-propanol, 2-ethoxyethanol, 2-isopropoxyethanol, 3-methoxy-3-methyl-1-butanol, tetrahydrofuran, n-propanol, t-butanol, 2-butoxyethanol, ethanol, isopropanol and acetonitrile, and subsequent crystallization from the solution.

In a preferable embodiment, a system consisting of isopropanol and water is used as the crystallization solvent. 50 to 90% (v/v) aqueous isopropanol solution is used as the crystallization solvent. The crystallization is conducted at a temperature of 0 to 20° C. The crystallization is preferably conducted at a temperature of 10° C. A solution of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid at a concentration of 7 to 10% (w/w) in solvent is used in crystallization. Crystals of (+)-(1R,5S,6S)-6-[(R)-1-hydroxyethyl]-1-methyl-2-[(2S,4S)-2-[(3R)pyrrolidine-3-yl-(R)-hydroxymethyl]pyrrolidine-4-yl]thio-1-carbapen-2-em-3-carboxylic acid monohydrochloride trihydrate are seeded in crystallization in an amount of about 3 to 5% (wt. %) based on the quantified amount of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid.

The resulting trihydrate crystals preferably have a powdery X-ray diffraction pattern containing lattice distances (d) of 9.0, 4.1 and 2.8 Å. The crystals further preferably have a powdery X-ray diffraction pattern containing lattice distances (d) of 9.0, 5.4, 5.2, 5.0, 4.1, 4.0, 3.8, 3.6, 3.4, 3.1, 2.8 and 2.6 Å.

The trihydrate crystals can also be obtained in another process. That is, the present invention provides a process for producing (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals, which comprises dissolving (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate crystals in 50 to 90% (v/v) aqueous isopropanol solution and subjecting the solution to crystallization at a temperature of 0 to 20° C.

The present invention also encompasses the above described monohydrate crystals. Further, the crystals have a powdery X-ray diffraction pattern containing lattice distances (d) of 9.4, 6.2, 5.4, 5.2, 4.8, 4.7, 4.4, 4.3, 4.0, 3.8, 3.6, 3.4 and 3.3 Å.

The monohydrate crystals can be obtained in the following manner. That is, the present invention provides a process for producing (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate crystals, which comprises dissolving (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid or a derivative thereof in a crystallization solvent in a methanol/water system, a dimethyl sulfoxide/water system, a dimethylformamide/water system, a 2-methoxyethanol/water system or a dimethylacetamide/water system and then crystallizing the compound.

In a preferable embodiment, the process for producing the monohydrate crystals makes use of a system consisting of methanol and water as the crystallization solvent. 50 to 90% (v/v) aqueous methanol solution is used as the crystallization solvent. A solution of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid at a concentration of 5 to 10% (w/w) in solvent is used in crystallization. The resulting monohydrate crystals are crystals having a powdery X-ray diffraction pattern containing lattice distances (d) of 5.2, 4.3 and 4.0 Å. The crystals further preferably have a powdery X-ray diffraction pattern containing lattice distances (d) of 9.4, 6.2, 5.4, 5.2, 4.8, 4.7, 4.4, 4.3, 4.0, 3.8, 3.6, 3.4 and 3.3 Å.

The monohydrate crystals can also be produced in another process. That is, the present invention provides a process for producing (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate crystals, wherein 50 to 90% (v/v) aqueous isopropanol solution is used as the crystallization solvent, and (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate crystals are added as nucleating crystals in an amount of at least 20% (wt. %) based on the quantified amount of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid. In a preferable embodiment, the crystallization is conducted at a temperature of 20 to 50° C. The crystallization is most preferably conducted at a temperature of 22° C.

In crystallization in production of the trihydrate crystals and monohydrate crystals, the carbapenem compound (free form, carboxylic acid form) or its derivative is dissolved as the starting material in solvent etc. The derivative is a salt, a hydrate or a salt hydrate. The salt includes e.g. ordinarily used salts such as hydrochloride, sulfate, acetate, phthalate, phosphate and oxalate. When the salt is other than hydrochloride, a hydrochloride forming agent such as calcium chloride may be used. Use can also be made of a derivative of the carbapenem compound whose substituent group has been replaced by another substituent group and which has the intended carbapenem skeleton in the step of crystallization.

In the crystallization step, salt formation and crystallization can also be carried out successively. The salt may be subjected to crystallization. Further, the monohydrate crystals can be formed into trihydrate crystals or the trihydrate crystals can be formed into monohydrate crystals.

Further, the present invention provides a powdery charged preparation for injection, which comprises (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid (referred to hereinafter as carbapenem compound) represented by the following formula 2:

(Formula 2)

a salt thereof, crystals of the salt, a hydrate of the salt, or hydrate crystals of the salt (referred to hereinafter as carbapenem derivatives) charged and capped in a vial.

Preferably, the air in the vial is partially or wholly removed and/or replaced by nitrogen or argon. The medicine is preferably in the form of hydrochloride trihydrate crystals having a powdery X-ray diffraction pattern containing lattice distances (d) of 9.0, 4.1 and 2.8 Å. The medicine may be hydrochloride monohydrate crystals having a powdery X-ray diffraction pattern containing lattice distances (d) of 5.2, 4.3 and 4.0 Å.

Further, the present invention provides a method of administering the above preparation, wherein the preparation is dissolved just before use in an injection liquid such as water and administered by injection into a patient immediately while the medicine is stable.

DETAILED DESCRIPTION OF THE INVENTION

First, the trihydrate and monohydrate crystals and the process for producing these crystals are described.

That is, the present invention relates to carbapenem monohydrochloride trihydrate crystals having a powdery X-ray diffraction pattern containing lattice distances (d) of 9.0, 4.1 and 2.8 Å, carbapenem monohydrochloride trihydrate crystals having a powdery X-ray diffraction pattern containing lattice distances (d) of 9.0, 5.4, 5.2, 5.0, 4.1, 4.0, 3.8, 3.6, 3.4, 3.1, 2.8 and 2.6 Å, a process for producing the above-mentioned monohydrochloride trihydrate crystals, which comprises using, as a crystallization solvent, a system consisting of water and a mixed solvent of one or more members selected from the group consisting of dimethyl ether, diethylene glycol monomethyl ether, triethylene glycol monomethyl ether, diethylene glycol monoethyl ether, 1-acetoxy-2-methyl ethane, 3-methoxybutanol, 1-ethoxy-2-propanol, 1-methoxy-2-propanol, 2-ethoxyethanol, 2-isopropoxyethanol, 3-methoxy-3-methyl-1-butanol, tetrahydrofuran, n-propanol, t-butanol, 2-butoxyethanol, ethanol, isopropanol and acetonitrile, the process for producing the above monohydrochloride trihydrate crystals, wherein a system consisting of isopropanol and water is used as the crystallization solvent, the process for producing the above monohydrochloride trihydrate crystals, wherein 50 to 90% (v/v) aqueous isopropanol solution is used as the crystallization solvent, the process for producing the above monohydrochloride trihydrate crystals, wherein crystallization is conducted at a temperature of 0 to 20° C., the process for producing the above monohydrochloride trihydrate crystals, wherein crystallization is conducted at a temperature of 10° C., the process for producing the above monohydrochloride trihydrate crystals, wherein a solution of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid at a concentration of 7 to 10% (w/w) in solvent is used in crystallization, the process for producing the above monohydrochloride trihydrate crystals, wherein crystals of carbapenem monohydrochloride trihydrate are seeded in crystallization in an amount of about 3 to 5% (wt-%) based on the quantified amount of the carbapenem compound, the process for producing the above monohydrochloride trihydrate crystals, wherein the crystals have a powdery X-ray diffraction pattern containing lattice distances (d) of 9.0, 4.1 and 2.8 Å.

Further, the present invention relates to a process for producing a monohydrochloride monohydrate crystals of carbapenem compound, which comprises using, as a crystallization solvent, a methanol/water system, a dimethyl sulfoxide/water system, a dimethylformamide/water system, a 2-methoxyethanol/water system or a dimethylacetamide/water system, the process for producing the above monohydrochloride monohydrate crystals, wherein a system consisting of water and isopropanol is used as the crystallization solvent, the process for producing the above monohydrochloride monohydrate crystals, wherein 50 to 90% (v/v) aqueous methanol solution is used as the crystallization solvent, the process for producing the above monohydrochloride monohydrate crystals, wherein a solution of the carbapenem compound at a concentration of 5 to 10% (w/w) in solvent is used in crystallization, the process for producing the above monohydrochloride monohydrate crystals, wherein 50 to 90% (v/v) aqueous isopropanol solution is used as the crystallization solvent, and the monohydrochloride monohydrate crystals are added as nucleating crystals in an amount of at least 20% (wt-%) based on the quantified amount of the carbapenem compound, the process for producing the above monohydrochloride monohydrate crystals, wherein crystallization is conducted at a temperature of 20 to 50° C., the process for producing the above monohydrochloride monohydrate crystals, wherein crystallization is conducted at a temperature of 22° C.

Further, it relates to a process for producing the above monohydrochloride trihydrate crystals, which comprises dissolving the above monohydrochloride monohydrate crystals in 50 to 90% (v/v) aqueous isopropanol solution and subjecting the solution to crystallization at a temperature of 0 to 20° C.

In any of the processes described above, the monohydrochloride trihydrate crystals can be crystals having a powdery X-ray diffraction pattern containing lattice distances (d) of 9.0, 4.1 and 2.8 Å.

Hereinafter, the present invention, as well as terms etc. used in this specification, is described in detail.

The compound of the present invention, that is, (+)-(1R, 5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals, is represented by the following formula:

The lattice distance (d) of the carbapenem monohydrochloride trihydrate crystals can be calculated from 2θ value in the scanning axis of each diffraction peak obtained in powdery X-ray diffraction evaluation. That is, the lattice distance (d) of the crystals can be determined from the Bragg equation ($1/d = 2\sin\theta/\lambda$, where $\lambda = 1.5418$ Å) on the basis of the θ value of each of major diffraction peaks.

Evaluation by powdery X-ray diffraction was conducted under the following measurement conditions using an instrument (INT-2500 Ultrax 18) manufactured by Rigaku Co., Ltd.
X-ray used: Cu K alpha ray
Counter: Scintillation counter
Goniometer: Vertical goniometer (RINT2000)
Applied voltage: 40 kV
Applied current: 200 mA
Scan speed: 2°/min
Scanning axis: 2θ
Scanning range: 2θ=5 to 30
Divergent slit: 1°
Scattering slit: 1°
Light receiving slit: 0.15 mm The (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals according to the present invention have a powdery X-ray diffraction pattern containing lattice distances (d) of preferably 9.9, 4.1 and 2.8 Å, more preferably 9.0, 5.4, 5.2, 5.0, 4.1, 4.0, 3.8, 3.6, 3.4, 3.1, 2.8 and 2.6 Å.

In the present invention, the carbapenem compound or its salt as an antibiotic to be first dissolved for crystallization can be produced in a usual manner or in a known organic chemical synthesis method. It can also be produced by methods described in e.g. JP-A 8-73462 and JP-A 11-35556.

The antibiotic hydrochloride hydrate crystals according to the present invention can be produced by the above known method in the following general scheme.

X=1 or 3 wherein PNB means a p-nitrobenzyl group.

Hereinafter, the conditions for crystallization are described in detail.

The carbapenem monohydrochloride trihydrate crystals according to the present invention can be produced under the following conditions.

The solvent used for crystallization of the trihydrate crystals is preferably a system consisting of water and a mixed solvent of one or more members selected from the group consisting of dimethyl ether, diethylene glycol monomethyl ether, triethylene glycol monomethyl ether, diethylene glycol monoethyl ether, 1-acetoxy-2-methyl ethane, 3-methoxybutanol, 1-ethoxy-2-propanol, 1-methoxy-2-propanol, 2-ethoxyethanol, 2-isopropoxyethanol, 3-methoxy-3-methyl-1-butanol, tetrahydrofuran, n-propanol, t-butanol, 2-butoxyethanol, ethanol, isopropanol and acetonitrile, more preferably a system consisting of water and a mixed solvent of one or more members selected from the group consisting of diethylene glycol monomethyl ether, diethylene glycol monoethyl ether, 1-ethoxy-2-propanol, 2-ethoxyethanol, 2-isopropoxyethanol, tetrahydrofuran, n-propanol, t-butanol, isopropanol and acetonitrile, more preferably a system consisting of water and a mixed solvent of one or more members selected from the group consisting of diethylene glycol monomethyl ether, 2-ethoxyethanol, tetrahydrofuran, t-butanol, isopropanol and acetonitrile, more preferably a system consisting of water and a mixed solvent of one or more members selected from the group consisting of diethylene glycol monomethyl ether and isopropanol, and most preferably an isopropanol/water system.

The mixing ratio of one or more organic solvents described above or the mixing ratio thereof to water is not particularly limited. The solubility of the antibiotic is increased as water is increased, and use can be made of an organic solvent at a concentration (v/v) of 1 to 95%, preferably 10 to 90%, further preferably 40 to 90%, more preferably 50 to 90%, and most preferably 55 to 85% in water. When an aqueous isopropanol solution is used as a crystallization solvent, e.g. 50 to 90% (v/v) aqueous isopropanol solution can be used.

The crystallization temperature is not particularly limited, but in consideration of the stability of the antibiotic, the temperature is preferably 20° C. or less, more preferably 0 to 20° C. and most preferably 10° C.

The concentration of the carbapenem compound in the mother-liquor solvent for precipitating crystals is not particularly limited either. The concentration is preferably 7 to 10% (w/w).

For crystallization, crystals of carbapenem monohydrochloride trihydrate can also be seeded, and the amount to be seeded is not particularly limited, but is preferably about 3 to 5% (wt-%), more preferably 3%, based on the quantified amount of the carbapenem compound.

The carbapenem monohydrochloride monohydrate crystals can be produced under the following conditions.

As the crystallization solvent for the monohydrate crystals, use can be made of a methanol/water system, a dimethyl sulfoxide/water system, a dimethylformamide/water system, a 2-methoxyethanol/water system or a dimethylacetamide/water system, preferably a methanol/water system, a dimethyl sulfoxide/water system, a dimethylformamide/water system, and most preferably a methanol/water system.

The mixing ratio thereof is not particularly limited. The solubility of the antibiotic is increased as water is increased, and use can be made of an organic solvent at a concentration (v/v) of 1 to 95%, preferably 10 to 90%, further preferably 40 to 90%, more preferably 50 to 90%, and most preferably 55 to 85% in water. The crystallization temperature is not particularly limited either.

For crystallization of the monohydrate crystals, 50 to 90% (v/v) aqueous isopropanol solution is used as the crystallization solvent to which carbapenem monohydrochloride monohydrate crystals can be seeded in an amount of at least 20% (wt-%) based on the quantified amount of the carbapenem compound. The ratio of isopropanol to water and the amount of crystals to be seeded can be suitably regulated, but the amounts described above are more preferable. The crystallization temperature is more preferably a temperature of 20 to 50° C. The temperature is more preferably 22° C.

The monohydrate crystals obtained as described above can be converted into trihydrate crystals for example by dissolving the monohydrate crystals in 50 to 90% (v/v) aqueous isopropanol solution followed by re-crystallization at a temperature of 0 to 20° C.

The carbapenem monohydrochloride trihydrate crystals according to the present invention are advantageous in that they are stable, can be kept easily for maintaining the qualities of the pharmaceutical preparation, can keep the qualities for a long period and can be easily purified by readily removing impurities in manufacturing. In particular, the trihydrate can be easily purified by removing impurities hardly separated from the monohydrate, and is thus industrially very useful.

Now, the monohydrate crystals are described.

The present invention relates to carbapenem monohydrochloride monohydrate crystals having a powdery X-ray diffraction pattern containing lattice distances (d) of 5.2, 4.3 and 4.0 Å, represented by the following structural formula 1:

(Formula 1)

Further, the present invention relates to carbapenem hydrochloride monohydrate crystals having an X-ray diffraction pattern containing lattice distances (d) of 9.4, 6.2, 5.4, 5.2, 4.8, 4.7, 4.4, 4.3, 4.0, 3.8, 3.6, 3.4 and 3.3 Å, represented by formula 1. The crystals are those characterized by having diffraction intensity in the lattice distances (d) of 19.4, 6.2, 5.4, 5.2, 4.8, 4.7, 4.4, 4.3, 4.0, 3.8, 3.6, 3.4 and 3.3 Å, particularly by having strong diffraction intensity in the three lattice distances (d) of 5.2, 4.3 and 4.0 Å.

The carbapenem hydrochloride monohydrate crystals are stable under heated and humidified conditions.

The carbapenem hydrochloride monohydrate crystals can also be obtained by crystallization from a mixed solvent of water and ethanol or isopropyl alcohol, followed by drying the resulting crystals. The hydrochloride monohydrate crystals can also be produced by crystallization from a mixed solvent of water and a poor solvent such as ethanol or isopropyl alcohol, followed by drying the resulting crystals until their water content is reduced to 3 to 8% (w/w), preferably 4 to 6% (w/w). The carbapenem hydrochloride or its monohydrate may be first dissolved in water and then crystallized by adding a poor solvent, or may from the start be dissolved in a mixed solvent of water and a poor solvent and then crystallized. In the case of dissolution in water and crystallization by adding a poor solvent, the solution temperature is kept desirably at 0 to 15° C., and for example the compound is dissolved under cooling on ice. Examples of the poor solvent include, but are not limited to, ethanol and isopropanol.

The mixing ratio of water/ethanol or isopropyl alcohol in the solvent used for precipitating the crystals of the present invention is 1 part by weight of water/0.1 to 100 parts by weight, preferably 5 to 20 parts by weight of ethanol or isopropanol. Examples of drying after crystallization include, but are not limited to, vacuum drying, drying in a nitrogen stream, drying in a dry air stream, and air-drying.

In the present invention, (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid, a salt thereof, another salt or another derivative to be first dissolved in the solvent for crystallization can be produced in a known method. For example, it can be produced by a method disclosed in JP-A 8-73462.

Further, the present invention relates to a powdery charged preparation for injection, which comprises (+)-(1R, 5S,6S)-6-[(R)-1-hydroxyethyl]-1-methyl-2-[(2S,4S)-2-[(3R)-pyrrolidine-3-yl-(R)-hydroxymethyl]pyrrolidine-4- yl]thio-1-carbapen-2-em-3-carboxylic acid hydrochloride monohydrate crystals having an X-ray diffraction pattern containing lattice distances (d) of 5.2, 4.3 and 4.0 Å, or lattice distances (d) of 9.4, 6.2, 5.4, 5.2, 4.8, 4.7, 4.4, 4.3, 4.0, 3.8, 3.6, 3.4 and 3.3 Å, or (+)-(1R,5S,6S)-6-[(R)-1-methyl-2-[(2S,4S)-2-[(3R)-pyrrolidine-3-yl-(R)-hydroxyethyl]-pyrrolidine-4-yl]thio-1-carbapen-2-em-3-carboxylic acid hydrochloride trihydrate crystals having an X-ray diffraction pattern containing lattice distances (d) of 9.0, 4.1 Å, or lattice distances of 9.0, 5.4, 5.2, 5.0, 4.1, 4.0, 3.8, 3.6, 3.4, 3.1, 2.8 and 2.6 Å charged and capped in a vial. That is, the hydrochloride monohydrate and trihydrate crystals according to the present invention are stable under heated and humidified conditions so that the crystals can be charged and capped in a vial to provide a stable powdery charged preparation.

The lattice distance (d) of (+)-(1R,5S,6S)-6-[(R)-1-hydroxyethyl]-1-methyl-2-[(2S,4S)-2-[(3R)-pyrrolidine-3-yl (R)-hydroxymethyl]pyrrolidine-4-yl]thio-1-carbapen-2-em-3-carboxylic acid hydrochloride monohydrate crystals can be calculated from 2θ value in the scanning axis of each diffraction peak obtained in powdery X-ray diffraction evaluation. That is, the lattice distance (d) of the crystals can be determined from the Bragg equation ($1/d = 2\sin\theta/\lambda$, where $\lambda = 1.5418$ Å) on the basis of the θ value of each of major diffraction peaks.

Further, the present invention relates to a powdery charged preparation for injection, which was subjected to degasification of a part or the whole of the air in a vial and/or replacement thereof by nitrogen or argon.

The (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid hydrochloride monohydrate and trihydrate crystals according to the present invention are superior in stability. However, due to a change in manufacturing conditions and a difference in production lot, the coloration of the outward appearance on the surface of the crystals may be recognized with time under heated conditions and/or humidified conditions. In this case, one feature of the present invention is that the coloration of the powdery charged preparation for injection can be prevented by 1) degassing a part or the whole of the air in a vial to remove a part or the whole of residual oxygen in the vial, 2) replacing a part or the whole of the air in a vial by nitrogen or argon, or 3) degassing a part or the whole of the air in a vial thereby removing a part or the whole of residual oxygen followed by replacement by nitrogen or argon.

Degasification of the air in the vial is conducted by e.g. an air suction device, a vacuum suction device etc., but is not particularly limited. When a part or the whole of the air in the vial is degasified to remove a part or the whole of residual oxygen, the pressure in the vial is desirably 100 hPa (hectopascal) or less, more desirably 10 hPa (hectopascal) or less. The oxygen concentration in the air in the vial is desirably 5% or less, more desirably 0.5% or less.

The powdery charged preparation for injection, comprising (+)-(1R,5S,6S)-6-[(R)-1-hydroxyethyl]-1-methyl-2-[(2S,4S)-2[(3R)-pyrrolidine-3-yl-(R)-hydroxymethyl]pyrrolidine-4-yl]thio-1-carbapen-2-em-3-carboxylic acid hydrochloride monohydrate and trihydrate crystals according to the present invention is advantageous in that the preparation is superior in stability, can be easily stored, and can maintain predetermined qualities for a long period from the viewpoint of maintenance of the qualities of the pharmaceutical preparation.

When the powdery charged preparation for injection according to the present invention is administered into human beings or animals, a series of production steps are conducted preferably under aseptic conditions.

Figure 8:
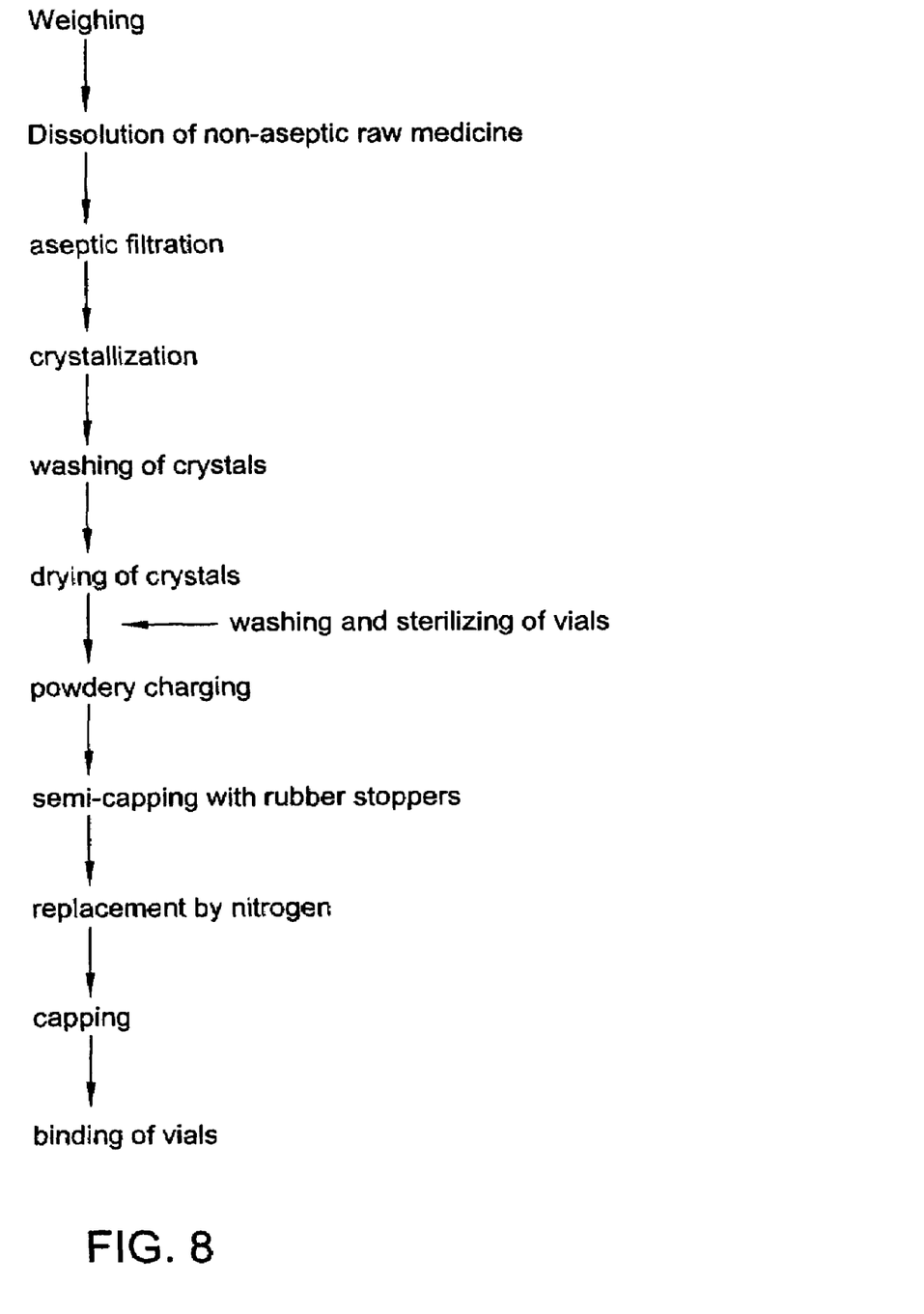
FIG. 8 shows an outline of the process for producing a powdery charged preparation for injection comprising (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]-thio-1-carbapen-2-em-3-carboxylic acid hydrochloride monohydrate and trihydrate.

By way of example, an outline of a process for producing the powdery charged preparation for injection according to the present invention is shown in FIG. 8. That is, (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid hydrochloride is weighed, dissolved in e.g. a mixed solvent of water and isopropyl alcohol, filtered aseptically with a filter, and crystallized from e.g. a mixed solvent of water and a poor solvent such as isopropyl alcohol. The resulting crystals are collected by filtration on a crystal filter, washed and dried, and the crystals are introduced in powdery form into vials previously washed and sterilized. Then, rubber stoppers are placed on the vials, and after the air in the vials is replaced by nitrogen, the vials are tightly capped with the rubber stoppers and finally bound with vial caps.

Further, the present invention relates to a powdery charged preparation for injection, which comprises (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen- 2-em-3-carboxylic acid represented by structural formula 2, a salt thereof, or hydrate crystals thereof charged and capped in a vial. The salt may be any acidic salts and includes, but is not limited to, hydrochloride, sulfate, acetate, phthalate and phosphate.

In the powdery charged preparation for injection using these crystals, a part or the whole of the air in the vial may be degasified so that a part or the whole of residual oxygen is removed or may be further replaced by nitrogen or argon.

The (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid hydrochloride monohydrate and trihydrate crystals according to the present invention can be used in various preparations to produce chemically stable preparations. That is, the crystals can be formed not only into the powdery charged preparation but also into stable lyophilized preparations (injections, oral agents) and stable oral preparations (tablets, granules, capsules etc.), which were crystallized in the step of freeze-drying.

Hereinafter, the present invention is described in more detail by reference to the Examples, which however are not intended to limit the present invention.

According to the present invention, there can be provided novel carbapenem hydrochloride hydrate crystals from which impurities can be easily separated. Examples of the effects thereof are described below.

According to the present invention, there can be provided a stable injection preparation of novel carbapenem hydrochloride. Examples of the effects thereof are described below.

EXAMPLES

Hereinafter, the present invention is described in more detail by reference to the Examples, which however are not intended to limit the present invention.

In Examples, hydrochloride hydrate crystals were produced in the following scheme as one example.

1. purification by SP850 column
2. concentration of main fr.
3. crystallization

1. CaCl₂
2. crystallization from IPA-H₂O

X=1 or 3 wherein PNB means the same group as defined above, and IPA means isopropyl alcohol.

Example 1-1

(+)-(1R,5S,6S)-6-[(R)-1-Hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate Reductive de-protection of p-nitrobenzyl (1R,5S,6s)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylate monoxalate (29.0 g; free form, 23.11 g, 42.3 mmol) was carried out in 2 steps as follows.

p-Nitrobenzyl (1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylate monoxalate (14.5 g), 20% palladium hydroxide-carbon (3.08 g, 50% wet material) and H₂O (333.5 mL) were introduced into a 500 mL four-necked flask equipped with a pH stat and a stirrer, and then suspended and stirred under cooling on a water bath (10° C.). After replacement by nitrogen was conducted 3 times, the mixture was vigorously stirred for 2.5 hours in a hydrogen atmosphere (hydrogen was supplied from a balloon at normal pressure), during which the pH of the reaction solution was kept at 5.5 by adding 1 N aqueous sodium hydroxide solution dropwise by a pump connected to the pH stat. When consumption of 1 N aqueous sodium hydroxide was stopped (total 24.5 mL), supply of hydrogen was stopped, and Celite (14.5 g) was introduced to it under stirring and stirred for 7 minutes. This suspension was combined with a Celite suspension obtained by carrying out the same reaction as above, and filtered under reduced pressure on a Buchner funnel having Celite (87 g) thereon, and the resulting cake was washed with H$_2$O (188 mL) to give an aqueous solution of the title compound (892.9 g). By quantification in HPLC, the resulting aqueous solution contained 13.2 g of the title compound in free form (yield, 75.8%).

The resulting aqueous solution was clarified by filtration (with a filter paper GA100; filtrate weight, 996.8 g), and a part (147.7 g) of the filtrate was treated with charcoal (0.66 g, Taiko FCS Co., Ltd.) for 10 minutes, and then the charcoal was filtered off (the title compound in free form; 1.881 g). An aqueous calcium chloride solution (5.76 g, 7.5% w/w) was added to the solution under ice-cooling and stirring, and charcoal in an amount (0.495 g) of 10% relative to the free compound was added thereto. After an additional aqueous calcium chloride solution (3.10 g, 7.0% w/w) was added thereto, the mixture was filtered through a Buchner funnel having 0.9 g Celite thereon to give a filtrate (174.8 g; the title compound in free form, 1.82 g). This aqueous solution was concentrated into 24 g concentrate, and water was added thereto to give 36 g solution. This solution was cooled to 10° C., and IPA (50 mL) was added thereto under stirring, and the mixture was seeded with crystals (0.08 g) of the title compound. After 15 minutes, precipitation of crystals was confirmed, and after aging for 1 hour, IPA (94 mL) was added dropwise thereto. After aging for 1 hour, the crystals were collected by filtration under suction, washed with 80% (v/v) aqueous IPA solution (20 mL) and then with acetone (10 mL), and dried under suction for 30 minutes in a nitrogen stream, to give 1.95 g of the title compound (free form, 1.61 g; yield, 85.5%).

Figure 1:
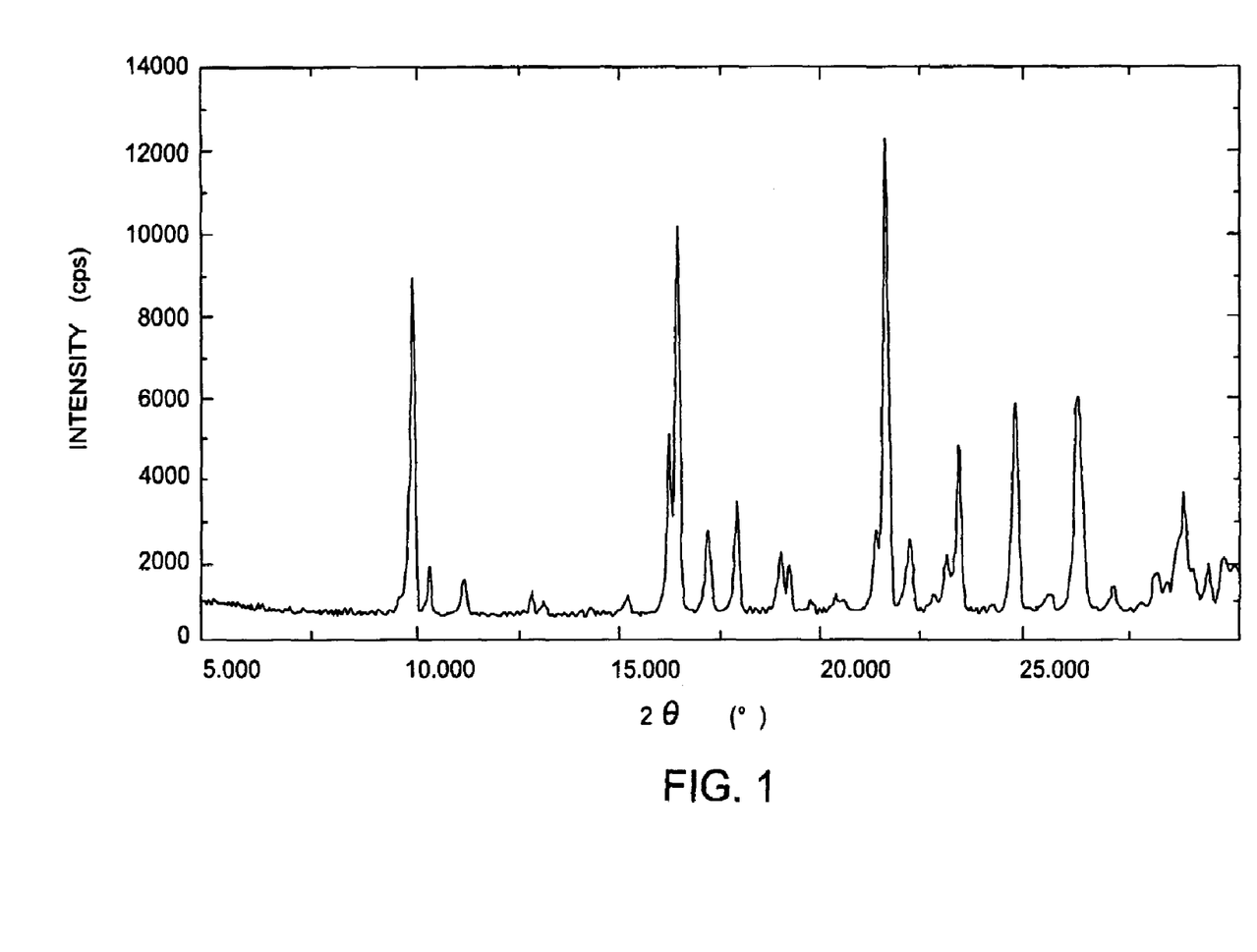
FIG. 1 shows a powdery X-ray diffraction pattern of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals.

The novel carbapenem hydrochloride crystals were evaluated by powdery X-ray diffraction (INT-2500 Ultrax 18, manufactured by Rigaku Co., Ltd.). FIG. 1 shows its powdery X-ray diffraction pattern.

Further, θ (°), lattice distance (d) and intensity (cps) of the major three characteristic peaks are shown in Table 1, and θ (°), lattice distance (d), intensity (cps) and relative intensity of the major peaks are shown in Table 2. The relative intensity of each peak was determined by the equation (relative intensity=intensity of each peak/intensity of maximum peak (d=4.0)).

TABLE 1

| 2 θ (°) | lattice distance (d) (Å) | intensity (cps) |
| --- | --- | --- |
| 9.8 | 9.0 | 7470 |
| 21.6 | 4.1 | 12113 |
| 32.0 | 2.8 | 3067 |

TABLE 2

| 2 θ (°) | lattice distance (d) (Å) | intensity (cps) | relative intensity* |
| --- | --- | --- | --- |
| 9.8 | 9.0 | 7470 | 62 |
| 16.4 | 5.4 | 9960 | 82 |
| 17.1 | 5.2 | 2682 | 22 |
| 17.8 | 5.0 | 3308 | 27 |
| 21.6 | 4.1 | 12113 | 100 |
| 22.2 | 4.0 | 2417 | 20 |
| 23.4 | 3.8 | 4617 | 38 |
| 24.7 | 3.6 | 5705 | 47 |
| 26.2 | 3.4 | 5857 | 48 |
| 28.7 | 3.1 | 3538 | 29 |
| 32.0 | 2.8 | 3067 | 25 |
| 34.6 | 2.6 | 2357 | 19 |

Example 1-2

(+)-(1R,5S,6S)-6-[(R)-1-Hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate (conversion of monohydrate to trihydrate)

1500 g aqueous solution of 174.4 g (free form, 150 g) of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate was introduced into a 10 L four-necked flask, and 1766 g of 2-propanol was added dropwise over 1 hour to this solution under stirring and cooling at 10° C. After it was confirmed that precipitation of crystals was initiated, the sample was aged for 1 hour, and 2944 g of 2-propanol (i.e. 81.6% (v/v) aqueous IPA in a 4-fold excess amount relative to the aqueous solution) was added dropwise thereto over 1 hour. After aging for 1 hour, the precipitated crystals were collected by filtration and washed with 750 mL of 80% (v/v) aqueous 2-propanol and then with 750 mL 2-propanol, and air-dried (1 hour) on a filter in a nitrogen stream under reduced pressure, to give 175.7 g desired trihydrate crystals (crystal yield, 96%). The powdery X-ray diffraction pattern of the resulting crystals with 11.6% water content agreed with that of trihydrate (FIG. 1). HPLC purity was 99.3%.

Example 1-3

(+)-(1R,5S,6S)-6-[(R)-1-Hydroxyethyl]-1-methyl-2-[2S,4S)-2-[(3R)-pyrrolidine-3-yl-(R)-hydroxymethyl]pyrrolidine-4-yl]-thio-1-carbapen-2-em-3-carboxylic acid monohydrochloride monohydrate Out of the solution (996.8 g) clarified by filtration with a glass filter (GA100) in Example 1-1, 849.1 g solution (free form: 10.79 g) was adjusted to pH 8.5 with 1 N aqueous sodium hydroxide, and the solution (871.4 g) was purified by applying it onto a resin (SP850) column (5 cmΦ×50 cm, flow rate of 50 mL/min, previously equilibrated with 0.05 M phosphate buffer). The column was charged with 20% aqueous methanol solution containing 0.05 M phosphate buffer, water and 1.0 equivalent of hydrochloric acid and then with 20% (v/v) aqueous methanol solution, and the resulting major fractions were stored overnight at 10° C. or less (yield, 81%). Out of the resulting solution (1985 g, containing 8.74 g free compound), 1621.1 g solution was concentrated into 125.2 g concentrate (containing 7.08 g free compound). Out of this concentrate, 93.9 g concentrate was discolored by adding 531 mg charcoal, and water was added to the filtrate to adjust the concentration of the free compound to 5% (weight of the solution: 102.67 g). This solution was further divided into 33.9 g (A) and 67.8 g (B).

While solution (A) was stirred at 22° C., 26.6 g of 2-propanol was added dropwise thereto over 1 hour, and monohydrate crystals, 0.4 g (corresponding to 20% (wt-%)

relative to the quantified amount of the free compound (+)-(1R,5S,6S)-6-[(R)-1-hydroxyethyl]-1-methyl-2-[(2S, 4S)-2-[(3R)-pyrrolidine-3-yl-(R)-hydroxymethyl]pyrrolidine-4-yl]thio-1-carbapen-2-em- 3-carboxylic acid) were added thereto as nucleating crystals. After precipitation of crystals was confirmed, the suspension was aged for 1 hour, and then a mixture of 53.2 g of 2-propanol and solution (B) was added dropwise thereto at 22° C. over 1 hour. After aging for 30 minutes, 239 g of 2-propanol was added dropwise thereto over 1 hour and the mixture was aged at 10° C. overnight. The precipitated crystals were collected by filtration and washed with 30 mL 80% (v/v) aqueous 2-propanol solution, 30 mL 2-propanol and 30 mL acetone in this order. The crystals were air-dried for 1 hour in a nitrogen stream, to give 5.71 g of the desired monohydrate crystals (yield, 92%). HPLC purity was 99.8%. The powdery X-ray diffraction pattern agreed with that of the monohydrate in FIG. 2 in Example 2-1 described later.

Example 1-4

Figure 2:
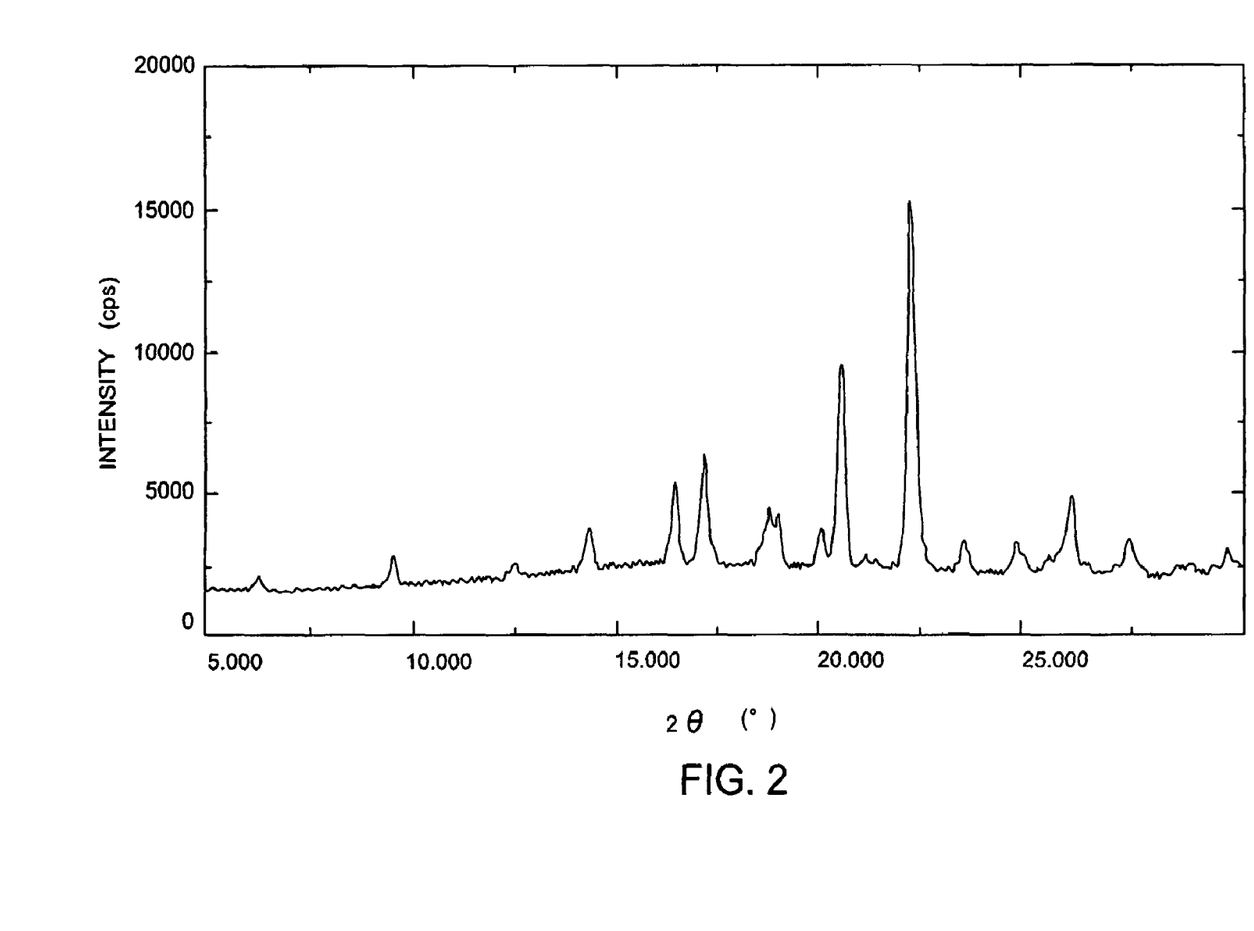
FIG. 2 shows a powdery X-ray diffraction pattern of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid hydrochloride monohydrate crystals.

(+)-(1R,5S,6S)-6-[(R)-1-Hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate 2.00 g (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate was dissolved at 20° C. in a mixed solvent of 8.0 ml distilled water and 6.0 ml methanol, then the insoluble matters were filtered off and 30 ml methanol was added dropwise thereto at 20° C. over 7 minutes under stirring. One hour after the dropwise addition was finished, the resulting crystals were collected by filtration. The crystals were washed with 5 ml methanol and air-dried for 1 hour in a nitrogen stream, to give 1.70 g of the desired monohydrate crystals (yield 85%). The powdery X-ray diffraction pattern is as shown in FIG. 2.

Example 1-5

Examination of the solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate and trihydrate in various aqueous organic solutions The solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate and trihydrate in various aqueous organic solvents at a concentration of 62.5% (v/v) in water at 20° C. was determined by HPLC in the following manner.

200 mg monohydrate crystals (or trihydrate crystals) were placed in a 30-ml two-necked flask, and 6.4 ml of 62.5% (v/v) organic solvent in water was added thereto and stirred with a stirrer at 20° C. for 30 minutes, and the solubility thereof was examined by quantification in HPLC. The results are shown in Table 3.

TABLE 3

| solvent | (mg/ml) | (mg/ml) |
|---|---|---|
| dimethyl ether | 1.93 | 1.44 |
| diethylene glycol monomethyl ether | 3.93 | 2.41 |
| triethylene glycol monomethyl ether | 2.86 | 2.47 |
| diethylene glycol monoethyl ether | 6.56 | 2.68 |
| 1-acetoxy-2-methyl ethane | 4.18 | 2.85 |
| 3-methoxybutanol | 4.39 | 3.24 |
| 1-ethoxy-2-propanol | 5.06 | 3.32 |
| 1-methoxy-2-propanol | 4.12 | 3.37 |
| 2-ethoxyethanol | 6.74 | 4.36 |
| 2-isopropoxyethanol | 6.03 | 4.36 |
| dimethyl acetamide | 4.06 | 4.53 |
| IPA (isopropyl alcohol) | 6.31 | 4.74 |
| 3-methoxy-3-methyl-1-butanol | 5.93 | 4.86 |
| tetrahydrofuran | 7.22 | 5.29 |
| 2-methoxyethanol | 5.37 | 6.39 |
| dimethyl formamide | 5.03 | 7.31 |
| n-propanol | 12.33 | 10.46 |
| t-butanol | 8.65 | 6.06 |
| dimethyl sulfoxide | 7.50 | 11.84 |
| 2-butoxyethanol | 13.29 | 11.85 |
| acetonitrile | 15.75 | 12.99 |
| ethanol | 6.60 | 6.32 |
| methanol | 10.22 | 14.38 |

From these results, the crystallization solvent for the monohydrate crystals is preferably a methanol/water system, a dimethyl sulfoxide/water system, a dimethylformamide/water system, a 2-methoxyethanol/water system or a dimethylacetamide/water system, and the crystallization solvent for the trihydrate crystals is preferably a system consisting of water and a mixed solvent of one or more members selected from the group consisting of dimethyl ether, diethylene glycol monomethyl ether, triethylene glycol monomethyl ether, diethylene glycol monoethyl ether, 1-acetoxy-2-methyl ethane, 3-methoxybutanol, 1-ethoxy-2-propanol, 1-methoxy-2-propanol, 2-ethoxyethanol, 2-isopropoxyethanol, 3-methoxy-3-methyl-1-butanol, tetrahydrofuran, n-propanol, t-butanol, 2-butoxyethanol, ethanol, isopropanol and acetonitrile.

Example 1-6

Examination of the solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate and trihydrate in aqueous MeOH The solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate and trihydrate in aqueous MeOH was examined in aqueous MeOH at a concentration (v/v) ranging from 54 to 84% at a temperature ranging from 4 to 40° C. in the same manner as in Examples 1 to 5.

Figure 3:
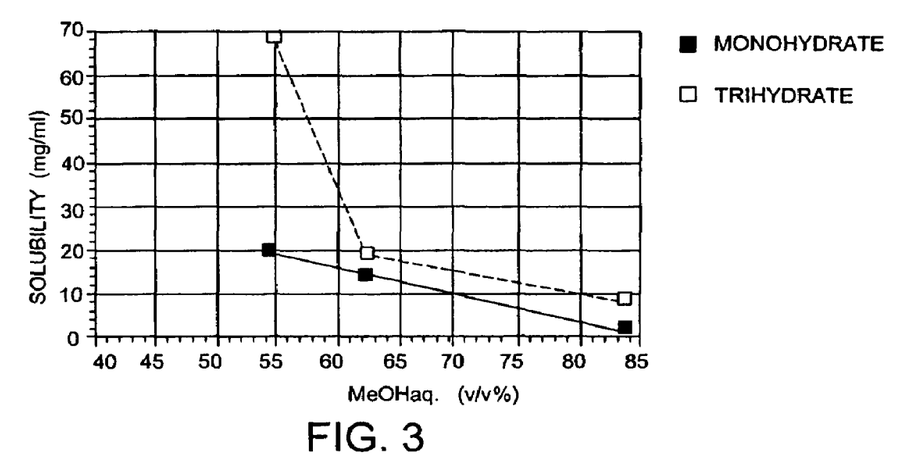
FIG. 3 shows the solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate (■) and trihydrate (□) in aqueous MeOH at 40° C.
Figure 4:
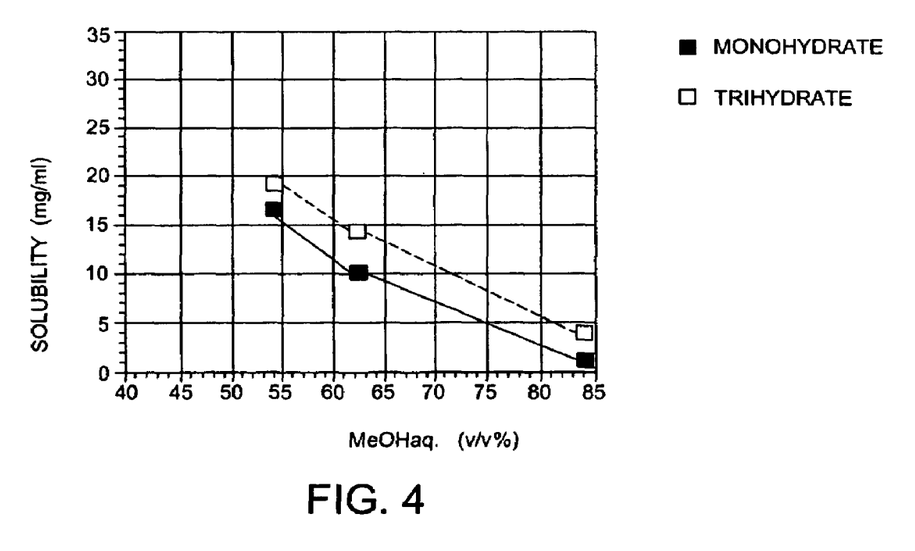
FIG. 4 shows the solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate (■) and trihydrate (□) in aqueous MeOH at 20° C.
Figure 5:
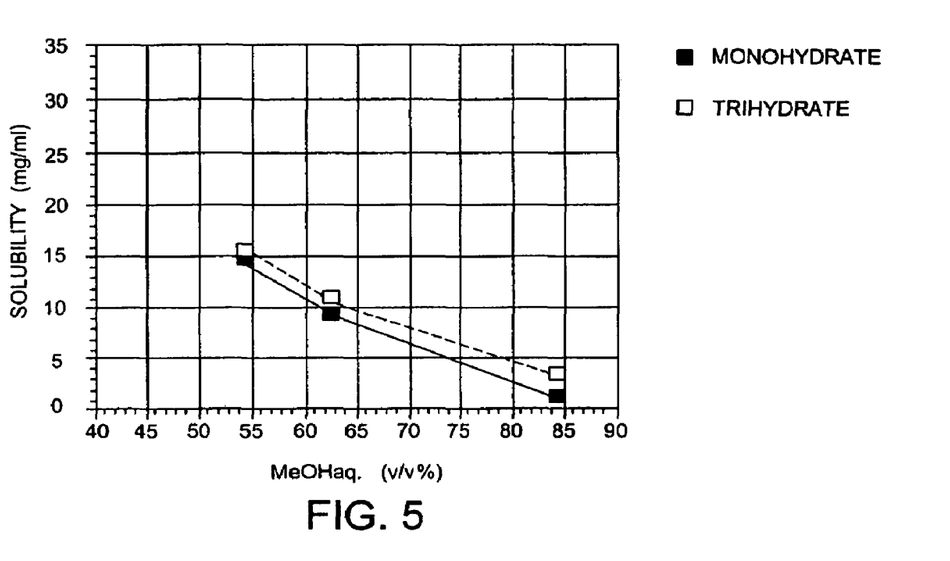
FIG. 5 shows the solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate (■) and trihydrate (□) in aqueous MeOH at 10° C.
Figure 6:
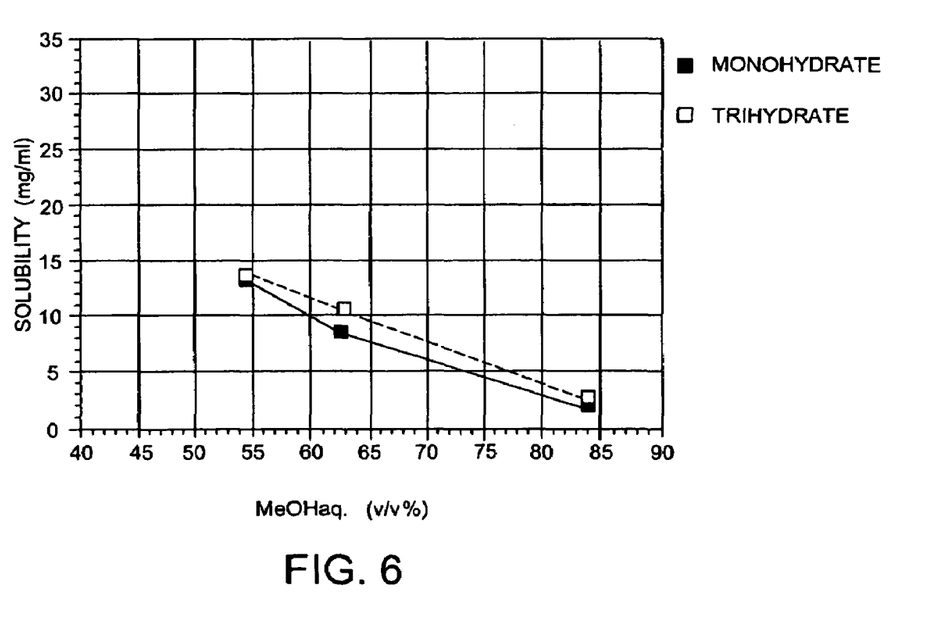
FIG. 6 shows the solubility of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride monohydrate (■) and trihydrate (□) in aqueous MeOH at 4° C.
Figure 7:
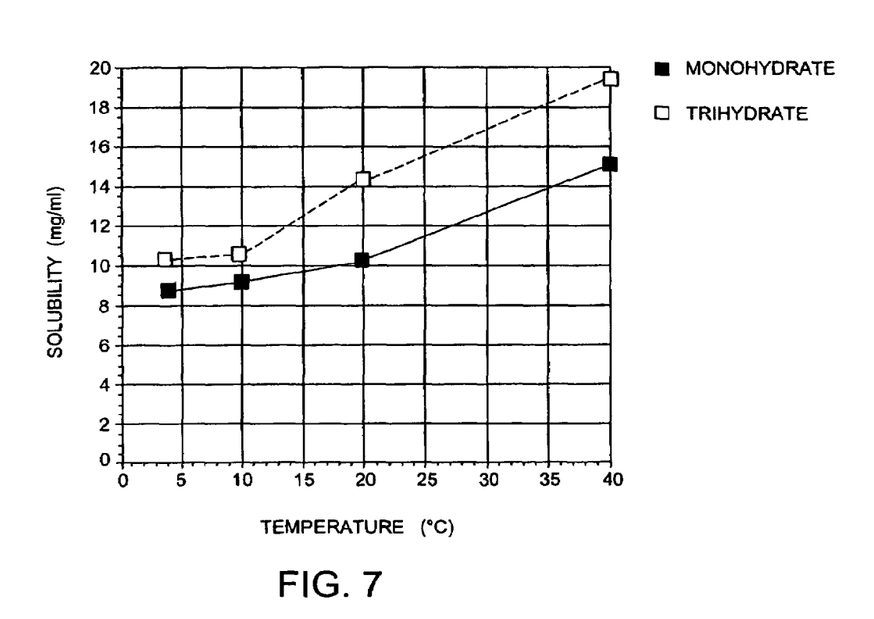
FIG. 7 shows the solubility of (+)-(1R,5S,6S)-6-[(R)-1-hydroxyethyl-1-methyl-2-[(2S,4S)-2-(3-yl-R)-pyrrolidine-3-yl-(R)-hydroxymethyl]pyrrolidine-4-yl]thio-1-carbapen-2-em-3-carboxylic acid monohydrochloride monohydrate (■) and trihydrate (□) in 62.5% (v/v) aqueous MeOH a teach temperature.

The results are shown in FIG. 3 (at 40° C.), FIG. 4 (at 20° C.), FIG. 5 (at 10° C.), FIG. 6 (at 4° C.) and FIG. 7 (at 62.5% (v/v) aqueous MeOH). The solubility of the monohydrate is expressed as "■" while the solubility of the trihydrate is expressed as "□". It can be seen that the monohydrate and trihydrate can be separately produced in such a wide range.

Example 1-7

Aseptic crystallization of a trihydrate preparation

Water for injection was added to 2000 g titer equivalent amount of novel non-aseptic carbapenem hydrochloride derivative to give 20 kg dispersion. This dispersion was stirred and dissolved under ice-cooling to prepare a charge solution. Thereafter, the solution was aseptically filtered through a 0.2 μm membrane filter (MCGL20S03, 0.2 μm, Millipore) and fed to a crystallization tank (equipped with a jacket). Then, the crystallization tank was stirred by bubbling with nitrogen at 0 to 15° C., and 25 L isopropyl alcohol was aseptically added thereto. After crystallization, 55 L isopropyl alcohol was added aseptically added thereto over 1 hour or so. After aging for a predetermined time, the precipitated crystals were collected aseptically by filtration. The crystals were washed with isopropyl alcohol and acetone, and dried in a nitrogen stream with regulated humidity (20 to 40 RH %) for 10 hours or more, to give novel aseptic carbapenem hydrochloride trihydrate crystals.

Example 1-8

The crystals obtained in Example 1-7 were divided and charged in an aseptic environment into sterilized glass vials (25 mg/vial, 50 mg/vial, 100 mg/vial, 150 mg/vial, 180 mg/vial, 200 mg/vial), then sealed with sterilized rubber stoppers and bound with aluminum caps to give powdery charged preparations for injection comprising the novel carbapenem hydrochloride crystals.

Example 1-9

The crystals obtained in Example 1-7 were divided and charged in an aseptic environment into sterilized glass vials (25 mg/vial, 50 mg/vial, 100 mg/vial, 150 mg/vial, 180 mg/vial, 200 mg/vial) by a weigh automatic micro-powder-filling machine (Ikeda Kikai Co., Ltd.), then sealed with sterilized rubber stoppers and bound with aluminum caps to give powdery charged preparations for injection comprising the crystalline powder of the carbapenem derivative.

Example 2-1

Monohydrate crystals were obtained in the same manner as in Example 1-3. The crystals were evaluated by powdery X-ray diffraction (INT-2500 Ultrax 18, manufactured by Rigaku Co., Ltd.).

The diffraction pattern thereof is as shown in FIG. 2.

Further, θ (°), lattice distance (d) and intensity (cps) of the major three characteristic peaks are shown in Table 4, and θ (°), lattice distance (d), intensity (cps) and relative intensity of the major peaks are shown in Table 5. The relative intensity of each peak was determined by the equation (relative intensity=intensity of each peak/intensity of maximum peak (d=4.0)).

TABLE 4

| 2 θ (°) | lattice distance (d) (Å) | intensity (cps) |
|---|---|---|
| 17.1 | 5.2 | 6496 |
| 20.2 | 4.3 | 10342 |
| 22.3 | 4.0 | 17317 |

TABLE 5

| 2 θ (°) | lattice distance (d) (Å) | intensity (cps) | relative intensity* |
|---|---|---|---|
| 9.4 | 9.4 | 2717 | 86.5 |
| 14.2 | 6.2 | 3708 | 118.0 |
| 16.3 | 5.4 | 5512 | 175.4 |
| 17.1 | 5.2 | 6496 | 206.7 |
| 18.7 | 4.8 | 4162 | 132.5 |
| 18.9 | 4.7 | 4179 | 133.0 |
| 20.0 | 4.4 | 3500 | 111.4 |
| 20.5 | 4.3 | 10342 | 329.2 |
| 22.3 | 4.0 | 17317 | 551.1 |
| 23.5 | 3.8 | 3142 | 100.0 |
| 24.8 | 3.6 | 2904 | 92.4 |
| 26.1 | 3.4 | 4529 | 144.1 |
| 27.3 | 3.3 | 3042 | 96.8 |

Example 2-2

The crystals obtained in Example 2-1 were divided and charged in an aseptic environment into sterilized glass vials (25 mg/vial, 50 mg/vial, 100 mg/vial, 150 mg/vial, 180 mg/vial, 200 mg/vial), then sealed with sterilized rubber stoppers and bound with aluminum caps to give powdery charged preparations for injection comprising the novel carbapenem hydrochloride crystals.

Example 2-3

The crystals obtained in Example 2-1 were divided and charged in an aseptic environment into sterilized glass vials (25 mg/vial, 50 mg/vial, 100 mg/vial, 150 mg/vial, 180 mg/vial, 200 mg/vial) by a weigh automatic micro-powder-filling machine (Ikeda Kikai Co., Ltd.) and then semi-capped with sterilized rubber stoppers, and after the air in the vials was replaced by nitrogen, the vials were sealed with the rubber stoppers and bound with aluminum caps, to give powdery charged preparations for injection comprising the crystalline powder of the carbapenem derivative.

Example 2-4

900 g of the raw medicine, that is, the novel non-aseptic carbapenem hydrochloride was weighed and dissolved in 8500 g distilled water for injection (WFI) under ice-cooling to prepare a charge solution, and then aseptically filtered through a 0.2 μm membrane filter (MCGL10S03, 0.2 μm, Millipore). Then, 40 L ethyl alcohol was added to the filtrate in a crystallization tank (equipped with a jacket) under aseptic conditions, and crystals were precipitated at 5° C. under stirring with a magnetic stirrer under bubbling with nitrogen. Then, the novel carbapenem trihydrate crystals were collected by a crystal filter and dried with dry air until their ethyl alcohol content was reduced to 1% or less. Thereafter, the crystals were divided and charged into vial vessels (50 mg/vial, 100 mg/vial) in an aseptic environment, sealed with sterilized rubber stoppers and bound with aluminum caps, to give powdery charged preparations for injection comprising the novel carbapenem hydrochloride crystals.

Experimental Examples

1) Stabilization Effect by the Powdery Charge Preparation for Injection 250 mg carbapenem hydrochloride was dissolved in 10 mL distilled water for injection to prepare an aqueous injection. The pH value of this aqueous injection was 5.04.

As the injection to be dissolved just before use, a freeze-dried preparation was prepared in the following manner. 3.5 g carbapenem hydrochloride, 456 mg sodium chloride and 2.815 g lactose were dissolved in 250 mL distilled water for injection. This solution was introduced into 2 mL glass vials (0.25 ml/vial), which were then semi-capped with rubber stoppers and freeze dried for 1 day. After it was confirmed that the samples were dried, the vials were fully capped and bound with aluminum caps.

As the powdery charged preparation of the amorphous raw medicine, a carbapenem hydrochloride compound prepared in the method described in JP-A 8-73462 was used.

As the crystalline powdery charged preparation of monohydrate crystals, the preparation (25 mg/vial) obtained in Example 2-2 was used. Further, as the crystalline powdery charged preparation of trihydrate crystals, the preparation (25 mg/vial) obtained in Example 1-8 was used.

These 5 preparations for injection were examined as follows: The aqueous injection was stored at 25° C. for 24, hours, and the freeze-dried preparation and the powdery charged preparations were stored at 40° C. under 75% relative humidity for the content of the novel carbapenem hydrochloride by high performance liquid chromatography. The content of the residual carbapenem compound in each preparation relative to the content (=100%) in the counterpart preparation stored in the cold place is shown in Table 6.

TABLE 6

| | | Stability test | |
|---|---|---|---|
| preparation form | crystalline state | Storage conditions | content of residual carbapenem compound (%) |
| aqueous injection | — | 25° C. for 24 hours | 87.2 |
| freeze-dried preparation | amorphous | 40° C.-75% RH for 1 month | 95.3 |
| powdery charged preparation | amorphous | 40° C.-75% RH for 1 month | 73.5 |
| powdery charged preparation (monohydrate) | crystal form | 40° C.-75% RH for 1 month | 100.3 |
| powdery charged preparation (trihydrate) | crystal form | 40° C.-75% RH for 1 month | 100.2 |

As is evident from the result of content stability in Table 6, the powdery charged preparation of the novel carbapenem hydrochloride crystals according to the present invention is a very stable preparation for injection as compared with the amorphous powdery charged preparation for injection and other preparations for injection (aqueous injection and lyophilized product).

2) Effect of Degasification of the Air in a Vial and/or Replacement Thereof by Nitrogen As the monohydrate crystals, the powdery charged preparation of the novel carbapenem hydrochloride crystals (25 mg/vial) obtained in the method in Example 2-3 (replacement by nitrogen), the powdery charged preparation (25 mg/vial) subjected to replacement by oxygen in place of replacement by nitrogen in Example 2-3, and the powdery charged preparation (25 mg/vial) not subjected to replacement in Example 2-2 were stored at 60° C. for 5 days (N=3) and then measured for their color difference ($\Delta E$), water content, powdery x-ray diffraction pattern, content of residual carbapenem and HPLC impurities. As the trihydrate crystals, the powdery charged preparation of the novel carbapenem hydrochloride crystals (25 mg/vial) obtained by the method (replacement by nitrogen) in Example 1-9 and the powdery charged preparation (25 mg/vial) not subjected to replacement in Example 1-8 were stored at 40° C. for 1 month and then measured for their color difference ($\Delta E$), water content and content of residual carbapenem. The color difference was evaluated by a color difference meter (ZE-200, Nippondenso Co., Ltd.); the water content by a Karl-Fisher moisture meter (CA-05, Mitsubishi Kagaku Kogyo); the powdery X-ray diffraction under the method and conditions in Example 1-1 or 2-1; and the content of residual carbapenem and HPLC impurities by high performance liquid chromatography (Shimadzu Corporation). The color difference ($\Delta E$) is a parameter indicative of a change in the color of the outward appearance of crystals, and its higher value indicates a greater coloration change than at an initial stage (just after production). The results of the monohydrate and trihydrate are shown in Tables 7 and 8, respectively.

TABLE 7

| | initial stage | |
|---|---|---|
| | water content (%) | HPLC impurity (%) |
| | 5.99 | 1.03 |

| gas for replacement | oxygen content (%) | color difference ($\Delta E$) | water content (%) | powdery X-ray diffraction pattern | content of carbapenem (%) | residual compound mean (%) | HPLC (%) | impurity mean (%) |
|---|---|---|---|---|---|---|---|---|
| nitrogen | 0.99 | 4.23 | 5.80 | no change | 98.8 | 98.40 | 0.63 | 0.63 |
| | 0.59 | 4.57 | 5.78 | no change | 98.1 | | 0.63 | |
| | 0.61 | 5.23 | 5.77 | no change | 9.2 | | 0.64 | |
| oxygen | 85.3 | 12.7 | 5.78 | no change | 97.5 | 97.80 | 0.63 | 0.64 |
| | 85.6 | 12.14 | 5.77 | no change | 98.1 | | 0.64 | |
| | 86.8 | 11.46 | 5.75 | no change | 97.8 | | 0.64 | |
| control (air) | 20.6 | 10.48 | 5.87 | no change | 98.6 | 98.40 | 0.62 | 0.63 |
| | 20.6 | 11.21 | 5.87 | no change | 98.6 | | 0.64 | |
| | 20.6 | 10.41 | 5.93 | no change | 98.1 | | 0.64 | |

TABLE 8

Stability in storage at 40° C. for 1 month

| gas for replacement | color difference (ΔE) | water content (%) | content of residual carbapenem compound (%) |
|---|---|---|---|
| nitrogen | 0.00 | 11.3 | 100.2 |
| control (air) | 2.78 | 12.0 | 101.0 |

Regardless of which treatment was conducted, the powdery charged preparations charged with the novel carbapenem hydrochloride crystals were stable without any change in the water content, powdery X-ray diffraction pattern, content of residual carbapenem, and HPLC impurities. However, the color difference (ΔE) of the surface of the crystals subjected to replacement by nitrogen was reduced as compared with that of the crystals subjected to replacement by oxygen or not subjected to any replacement treatment. That is, a thermal change in the color on the surface of the crystals could be prevented by replacement by nitrogen.

It is evident that the stability of the powdery charged preparations for injection, particularly of their outward appearance, against heat (temperature) is improved by replacing a part or the whole of the air in the vial by nitrogen.

The novel carbapenem hydrochloride crystals were weighed in 25 mL wide-mouthed glass bottles (30 mg/bottle), and in the bottles without caps, the monohydrate was stored for 1 week at 40° C. at a relative humidity of 0%, 19.2%, 53% and 75%, and the trihydrate was stored for 2 weeks at 25° C. at a relative humidity of 11%, 33%, 51%, 75% and 93%. Then, the crystals were measured for their color difference (ΔE), water content, powdery X-ray diffraction pattern, and content of residual carbapenem. The monohydrate was also examined in the presence or absence of an oxygen absorbent (trade name: Ageless, produced by Mitsubishi Gas Chemical Co., Ltd.) during storage at each relative humidity. The oxygen absorbent makes oxygen-free conditions under which the preparation is placed. The results of the monohydrate and trihydrate are shown in Tables 9 and 10, respectively.

TABLE 9 initial stage

| water content (%) | HPLC impurity (%) |
|---|---|
| 5.49 | 0.93 |

| relative humidity (%) | oxygen absorbent | color difference (ΔE) | water content (%) | powdery X-ray diffraction pattern | content of residual carbapenem compound (%) |
|---|---|---|---|---|---|
| 0 | absence | 1.87 | 5.08 | no change | 101.1 |
| 19.2 | absence | 5.01 | 6.18 | no change | 99.9 |
| 53 | absence | 6.28 | 6.17 | no change | 100.6 |
| 75 | absence | 35.98 | 6.60 | no change | 99.8 |
| 0 | presence | 2.95 | 5.31 | no change | 100.3 |
| 19.2 | presence | 3.97 | 5.72 | no change | 100.5 |
| 53 | presence | 5.85 | 6.29 | no change | 102.0 |
| 75 | presence | 4.56 | 6.43 | no change | 100.8 |

TABLE 10 hygroscopicity (25° C., 2 weeks)

| | trihydrate crystals | | monohydrate crystals | |
|---|---|---|---|---|
| relative humidity (%) | water content (%) | powdery X-ray diffraction pattern | water content (%) | powdery X-ray diffraction pattern |
| 11 | 11.0 | no change | 5.0 | no change |
| 33 | 11.1 | no change | 5.6 | no change |
| 51 | 11.1 | no change | 5.9 | no change |
| 75 | 11.1 | no change | 6.2 | no change |
| 93 | 11.4 | no change | 8.4 | no change |

The powdery charged preparations charged with the novel carbapenem hydrochloride crystals indicated a slightly increasing water content as the relative humidity was increases at 40° C. or 25° C., but there was no significant change in the content of residual carbapenem and the powdery X-ray diffraction pattern. Regardless of whether the oxygen absorbent was present or not, there was no difference in the water content, the content of residual carbapenem, and the powdery X-ray diffraction pattern. However, the color difference (ΔE) was smaller in the presence of the oxygen absorbent than in the absence thereof under the same temperature condition. That is, the coloration change on the surface of the crystals by humidity could be prevented by deoxidation treatment.

It is evident that the stability of the powdery charged preparations for injection, particularly the stability of their outward appearance, against humidity is evidently improved by degasification of a part or the whole of the air in the vial and subsequent deoxidation treatment.

As the monohydrate, the powdery charged preparation for injection of the novel carbapenem hydrochloride crystals (25 mg/vial) obtained in Example 2-2, the powdery charged preparation for injection (25 mg/vial) obtained in Example 2-3 (replacement of the air in the vial by nitrogen), and as the trihydrate, the powdery charged preparation for injection of the novel carbapenem hydrochloride crystals obtained in Example 1-8 and the powdery charged preparation for injection obtained in Example 1-9 (replacement of the air in the vial by nitrogen) were stored for 1 week, 1 month, or 3 months in the cold place (5° C.), at 25° C., 60% relative humidity (25° C./60% RH), at 40° C., 75% relative humidity (40° C./75% RH), or at 60° C., and the change in the outward appearance of the crystals (coloration change) was visually evaluated. The results of the monohydrate and trihydrate are shown in Tables 11 and 12, respectively.

TABLE 11

| storage condition | vial no. | storage term | | |
|---|---|---|---|---|
| | | 1 week | 1 month | 3 months |
| Charged into vials replaced therein by nitrogen | | | | |
| 5° C. | 1 | − | − | − |
| | 2 | − | − | − |
| | 3 | − | − | − |
| | 4 | − | − | − |
| 25° C./60% RH | 1 | − | − | − |
| | 2 | − | − | − |
| | 3 | − | − | − |
| | 4 | − | − | − |
| 40° C./75% RH | 1 | − | − | ± |
| | 2 | − | − | ± |
| | 3 | − | − | ± |

TABLE 11-continued

| storage condition | vial no. | storage term | | |
|---|---|---|---|---|
| | | 1 week | 1 month | 3 months |
| | 4 | – | – | ± |
| 60° C. | 1 | ± | ± | |
| | 2 | ± | ± | |
| | 3 | ± | ± | |
| | 4 | ± | ± | |
| Charged into usual vials | | | | |
| 5° C. | 1 | – | – | – |
| | 2 | – | – | – |
| | 3 | – | – | – |
| | 4 | – | – | – |
| 25° C./60% RH | 1 | ± | ± | + |
| | 2 | ± | ± | + |
| | 3 | ± | ± | + |
| | 4 | ± | ± | + |
| 40° C./75% RH | 1 | + | + | ++ |
| | 2 | + | + | ++ |
| | 3 | + | + | ++ |
| | 4 | + | + | ++ |
| 60° C. | 1 | ++ | ++ | |
| | 2 | ++ | ++ | |
| | 3 | ++ | ++ | |
| | 4 | ++ | ++ | |

TABLE 12

| storage condition | vial no. | storage term: 1 month | |
|---|---|---|---|
| | | charged into vials replaced therein by nitrogen | charged into usual vials |
| 5° C. | 1 | – | – |
| | 2 | – | – |
| | 3 | – | – |
| | 4 | – | – |
| 25° C./60% RH | 1 | – | ± |
| | 2 | – | ± |
| | 3 | – | ± |
| | 4 | – | ± |
| 40° C./75% RH | 1 | – | + |
| | 2 | – | + |
| | 3 | – | + |
| | 4 | – | + |
| 60° C. | 1 | ± | ++ |
| | 2 | ± | ++ |
| | 3 | ± | ++ |
| | 4 | ± | ++ |

In the cold (5° C.), there was no change in the outward appearance regardless of whether nitrogen replacement was conducted or not, but it was recognized that under heating conditions (60° C.) or under humidified conditions (25° C./60% RH, 40° C./75% RH), the coloration change was reduced by replacement of the air in the vial by nitrogen.

It is evident that the stability of the powdery charged preparation for injection against heat (temperature) and the stability of the outward appearance against humidity are improved by replacement of a part or the whole of the air in the vial by nitrogen and subsequent deoxidation treatment.

As the monohydrate, the powdery charged preparations for injection of the novel carbapenem crystals (25 mg/vial) obtained by degasification of the air in the vial at 100, 10, 1, 0.1 and 0.01 hPa (hectopascal) respectively and subsequent replacement by nitrogen according to the method in Example 2-3 (replacement by nitrogen) were stored at 60° C. for 1 or 4 weeks (N=6) and then measured for their color difference (ΔE). The oxygen concentrations in the preparations in vials degasified at 100, 10, 1, 0.1, 0.01 hPa (hectopascal) were measured by an oxygen analyzer (RO-101, Iizima Kogyo). As the trihydrate, the powdery charged preparations of the novel carbapenem hydrochloride crystals (25 mg/vial) obtained in the method in Example 1-9 (replacement by nitrogen) were degasified in the same manner, stored at 80° C. for 1 week (N=6) and then measured for their color difference (ΔE). As the control, the powdery charged preparation of the novel carbapenem hydrochloride crystals (25 mg/vial) subjected to neither degasification nor replacement by nitrogen was used. The results of the monohydrate and trihydrate are shown in Tables 13 and 14, respectively.

TABLE 13

| pressure (hPa) | oxygen concentration (%) mean ± S.D. | color difference (ΔE) | |
|---|---|---|---|
| | | 1 week | 4 weeks |
| 100 | 3.01 ± 1.12 | 2.85 | 8.02 |
| 10 | 0.29 ± 0.08 | 2.40 | 5.69 |
| 1 | 0.24 ± 0.04 | 2.62 | 4.51 |
| 0.1 | 0.21 ± 0.01 | 2.28 | 4.98 |
| 0.01 | 0.24 ± 0.03 | 3.11 | 4.91 |
| control (n = 6) | | 7.37 | 14.94 |

TABLE 14

| pressure (hPa) | color difference (ΔE) 80° C./1 week |
|---|---|
| 100 | 4.90 |
| 10 | 3.92 |
| 1 | 3.62 |
| control (n = 6) | 10.06 |

After storage at 60° C. for 1 or 4 weeks or at 80° C. for 1 week, any of the powder charged preparations in the degassed vials indicated a smaller color difference (ΔE) on the surface of the crystals than that of the control preparation. Particularly by degassing the air in the vial at 10 hPa (hectopascal) or less, that is, at an oxygen concentration of 0.5% or less in the vial, a thermal change in the color on the surface of the crystals could be significantly prevented.

It is evident that the stability of the outward appearance of the powdery charged preparations for injection against heat (temperature) is improved by reducing the oxygen concentration in the air in the vial to 0.5% or less followed by replacement by nitrogen.

The invention claimed is:

1. A process for producing (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid monohydrochloride trihydrate crystals, which comprises dissolving (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid or a salt thereof in a solvent system consisting of water and isopropanol and adding (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic hydroxymethyl]pyrrolidine-4-yl]thio-1-carbapen-2-em-3-carboxylic acid monohydrochloride trihydrate as seed crystals in crystallization in an amount of about 3 to 5% by weight based on the quantified amount of (+)-(1R,5S,6S)-6-[(R)-1-hydroxyethyl]-1-methyl-2-[(2S,4S)-2-[(3R)-pyrrolidine-3-yl-(R)-hydroxymethyl]pyrrolidine-4-yl]thio-1-carbapen-2-em-3-carboxylic acid.

* * * * *